United States Patent [19]
Prahl et al.

[11] Patent Number: 5,607,854
[45] Date of Patent: Mar. 4, 1997

[54] **COMPOSITION FOR INDUCING MALOLACTIC FERMENTATION USING *LEUCONOSTOC OENOS* STRAINS ACCESSION NUMBERS DSM 7008-DSM 7015**

[75] Inventors: Claus Prahl, Graested; Jan C. Nielsen, Hundested, both of Denmark

[73] Assignee: Chr. Hansen A/S, Horsholm, Denmark

[21] Appl. No.: 39,317

[22] PCT Filed: Mar. 30, 1993

[86] PCT No.: PCT/DK93/00116

§ 371 Date: Jul. 2, 1993

§ 102(e) Date: Jul. 2, 1993

[87] PCT Pub. No.: WO93/20180

PCT Pub. Date: Oct. 14, 1993

Related U.S. Application Data

[63] Continuation-in-part of Ser. No. 864,823, Apr. 1, 1992, abandoned.

[51] Int. Cl.$^6$ .............................. C12G 1/00; C12N 1/00; C12N 1/20
[52] U.S. Cl. ........................ 435/252.1; 426/13; 426/15; 435/822; 435/853
[58] Field of Search ............................. 435/243, 252.1, 435/252.9, 260, 822, 853, 139, 145, 170; 426/13, 15

[56] References Cited

FOREIGN PATENT DOCUMENTS

| | | |
|---|---|---|
| 13009/92 | 10/1992 | Australia . |
| 0141878 | 5/1985 | European Pat. Off. . |
| 0523316 | 1/1993 | European Pat. Off. . |
| 2485037 | 12/1981 | France . |
| 89/06685 | 7/1989 | WIPO . |

OTHER PUBLICATIONS

Abstract, Dialog Information Services, File 5, Biosis, Dialog Accession No. 5324127, Biosis No. 81091434, 1986, pp. 539–545.

Abstract, Dialog Information Services, File 5, Biosis, Dialog Accession No. 5235886, Biosis No. 81003193, 1985, pp. 872–876.

Abstract, Dialog Information Services, File 5, Biosis, Dialog Accession No. 7430956, Biosis No. 89081975, 1990, pp. 23–32.

Abstract, Dialog Information Services, File 351, WPI, Dialog Accession No. 008250107, WPI Accession No. 90–137108/18, JP 2086765, 1988.

J. Silver, et al., "Control of Malolactic Fermentation in Wine. 2. Isolation and Characterization of a New Malolactic Organism", Am. J. Enol. Vitic., vol. 32, No. 1, 1981, pp. 64–72.

Krieger, B. et al., "Techniques for the Application of Starter Cultures Used for Melolactic Fermentation in Wine (Abstract)", *Food Biotechnol.*, 7: 484 (1990).

*Primary Examiner*—David M. Naff
*Assistant Examiner*—Deborah K. Ware
*Attorney, Agent, or Firm*—Foley & Lardner

[57] ABSTRACT

A method of inducing malolactic fermentation in wine or fruit juice by the direct inoculation of a concentrate of a starter culture containing a selected malolactically active bacterial strain or strains having the accession no. DSM 7008, DSM 7009, DSM 7010, DSM 7011, DSM 7012, DSM 7013, DSM 7014 and DSM 7015. Further, the strains are characterized as having a survival rate of at least 80% when introduced into a wine having a pH of 3.2 or lower and containing at least 25 mg $SO_2$ per L and at least 12 vol % ethanol. Also the strains are capable of starting malolactic fermentation when added directly to the wine or fruit juice at a concentration of less than $10^7$ colony forming units per mL.

5 Claims, 10 Drawing Sheets

COMPOSITION FOR INDUCING MALOLACTIC FERMENTATION USING *LEUCONOSTOC OENOS* STRAINS ACCESSION NUMBERS DSM 7008-DSM 7015

RELATED APPLICATIONS

This application is a continuation-in-part of application Ser. No. 07/864,823, filed Apr. 1, 1992, now abandoned.

FIELD OF INVENTION

The present invention provides a novel method of inducing the decarboxylation of malic acid to lactic acid in wine or fruit juice by direct inoculation with a non-activated starter culture of malolactically active lactic acid bacteria and a composition comprising bacteria useful in the method.

BACKGROUND OF THE INVENTION

Grape juice, must and other fruit juice contain a varying amount of L-malic acid and L-malate, the amount typically being in the range of 1 to 10 g/L. The amount of malic acid and malate depends largely on the climatic conditions prevailing in the viticultural region. Hence, wines produced in colder areas tend to have a relatively higher acid content, since the malic acid is not degraded during the normal alcoholic fermentation. From a taste and flavour point of view, malic acid is considered undesirable in most red wines and in several types of rosé wines, white wines or sparkling wines.

However, the content of malic acid and malate in a wine may be reduced by a so-called malolactic fermentation (MLF) of the wine which fermentation results from the metabolic activity of various lactic acid bacteria, including species belonging to the genera of Lactobacillus, Pediococcus and Leuconostoc. Such bacteria may be present in must and wine as part of the indigenous microbial flora hereof, or they may have been added as a bacterial starter culture. Typically, the MLF is associated with malolactic bacterial growth and catabolic processes during which the wine acidity is reduced. The catabolic phase is usually entered when the malolactically active bacteria during the growth phase has reached a population density of about $10^6$ colony forming units (CFU) per mL. The microbial malolactic deacidification results from the decarboxylation of the dicarboxylic acid, L-malic acid to the monocarboxylic acid, L-lactic acid. As a result of this malolactic fermentation, the acidity of the wine decreases and the pH increases, resulting in a wine with a softer palate relative to that of the wine before the malolactic fermentation. Following a successful malolactic fermentation in wine, no further microbial growth will normally occur and hence, the wine is considered to be microbiologically stable.

The malolactic fermentation may occur spontaneously in the wine as a result of the growth of an indigenous flora of malolactically active lactic acid bacteria originating from the vines and grape skins and also often surviving from one season to the next on winery equipment, especially wooden casks or other equipment made of wood. When occurring in this fashion, malolactic fermentation is often delayed and may take place several months after the alcoholic fermentation. The initial number of bacteria is often quite small and the environment of the wine is frequently rather hostile to the growth of these bacteria due to the content of ethanol and sulphur dioxide in the wine, as well as its low pH and low nutrient concentration. The extended lag phase of the malolactic bacteria during which the wine is biologically unstable may result in the growth of bacteria producing volatile acidity and hence spoilage of the wine. Apart from this, certain indigenous malolactic bacteria spontaneously growing in the wine may produce certain compounds, e.g. biogenic amines that are believed to give rise to health problems.

In the traditional winery industry where the spontaneously occurring malolactic fermentation is being relied upon, it is common practice to stimulate malolactic fermentation by reducing the amount of added sulphur when determined as sulphur dioxide, to below 50 mg per L, delaying the removal of the lees, increasing the temperature of the wine to above 20° C., or ensuring a pH of more than 3.4. These measures, however, may also favour the growth of undesired microorganisms in the wine such as Acetobacter species, thus increasing the likelihood of wine spoilage, and this approach therefore requires extremely careful supervision of the decarboxylation process. Even if precautions are taken to enhance spontaneous MLF, this process is still difficult, not to say impossible, to control, and its occurrence has become even more unpredictable as winery hygiene has improved e.g. as a result of the replacement of wooden casks with stainless steel tanks. Such hygienic measures serve to ensure a uniform quality of the wine and reduce the risk of spoilage. However, they also reduce the chance of spontaneous conversion of malic acid taking place in the wine.

For this reason, and because the winemaker will often prefer to exercise a greater degree of control over the malolactic fermentation process it has become increasingly common practice in the winery industry to add a starter culture of malolactically active bacteria to the wine after the alcoholic fermentation. Presently, such a postfermentation malolactic fermentation in wine may be induced in different ways.

Currently, a widely practiced method of inducing MLF is to seed a wine with a small proportion of another wine already undergoing MLF and thus containing a high number of viable malolactically active bacteria. The culture in the seed wine is then already well adapted to wine conditions and will usually be capable of completing the malolactic fermentation in the seeded wine. However, this method of inoculation is rather tedious and not completely controllable. Thus, the method requires that a concentrated "mother culture" of the bacteria is propagated for an extended period of time, such as about two months, in diluted wine or grape juice, optionally after rehydration and/or adaptation of the mother culture in e.g. a grape fruit juice-containing medium which is then used to inoculate the wine to be used as a bulk starter culture in the form of seed wine. Typically, the wine is inoculated with the seed wine at a rate of 1 to 10 vol %, and accordingly, this method requires substantial investments in propagation equipment and adequately trained staff. In addition, it is difficult to control the propagation process and hence serious timing problems may occur. Should both red and white wine starter cultures be required these problems are doubled.

Relative to the above practice of using a seed wine, a postfermentation inoculation of wine with concentrated freeze-dried or frozen starter cultures of malolactically active lactic acid bacteria implies considerable savings in time and labour by substantially reducing the amount of scale-up work required. Such concentrated starter cultures are now commercially available and their use is being increasingly accepted in the wine industry, although their malolactic effect is not completely reliable. These culture compositions may be concentrated to contain a number of colony forming units which, when determined in a non-inhibitory medium is in the range of $10^9$ to $10^{11}$ per g of culture.

However, the use of known, commercially available malolactically active culture compositions contain bacteria which are susceptible to the conditions (low pH, content of $SO_2$, content of ethanol) prevailing in the fermented wine and accordingly, their malolactic efficiency requires that they become adapted to the hostile conditions in the wine by a carrying out a thawing and rehydration step (if freeze-dried), a thawing step (if frozen) and an activation step prior to inoculation in the wine. This requirement is assumingly due to the well-known phenomenon that a freeze-dried or frozen lactic acid bacterial culture composition, even if it includes additives protecting the bacteria against cell damages, will as a result of the freezing and/or freeze-drying process have an increased susceptibility to low pH, $SO_2$, ethanol and low temperatures as compared to a freshly grown culture of the same species.

If not rehydrated and activated as described above, the survival rate of the known commercial malolactic compositions on direct inoculation into wine will typically be in the range of 0.01 to 1% or even lower. Furthermore, the initially surviving non-adapted bacteria may gradually loose their viability in the wine.

Typically, this required adaptation comprises an initial thawing and/or rehydration process, the latter comprising dissolving the freeze-dried composition in water and adding various nutrients such as a sugar, vitamins, minerals or yeast extract and keeping the resulting solution at about 22° C. for about one hour. Subsequently, the thus rehydrated composition is subjected to an activation step, typically lasting 48 to 84 hours, in a medium which typically comprises grape juice or wine diluted with water, yeast extract, trace elements and vitamins. Normally, the number of CFUs does not increase during this activation period, on the contrary, the number may decrease. Even if the starter culture composition is adapted as described above, a varying proportion of adapted bacteria may loose viability as determined in a non-inhibitory medium when inoculated in wine. This loss of viability may be up till 90% of the added number of CFUs.

In EP-A1-0141878 is disclosed a method of reducing malic acid to lactic acid in wine by the introduction of high numbers of bacterial cells into the wine, which method comprises activating a concentrate of a bacterial culture in a nitrogen source-augmented fruit juice to form an activated mixture of bacteria containing at least about $10^5$ CFUs per mL and introducing the activated mixture into wine or grape must and converting the malic acid to lactic acid. The activation conditions disclosed are an activation period of 48 hours at 24° C.

Krieger et al. (Food Biotechnol. 1990, 7, 484) have disclosed the application in wine of malolactically active strains of *Leuconostoc oenos* and Lactobacillus spp. in the form of fresh or frozen concentrates using direct inoculation, i.e. without preceding activation, of at least $10^7$ CFUs per mL which concentration is indicated as being necessary to start malolactic fermentation. However, the application of such a high concentration of malolactictically active organisms is not commercially feasible in the wine industry due to the high cost of starter cultures. The necessity to apply at least $10^7$ CFUs per mL as disclosed in order to start MLF may indicate that the survival rate of these organisms when applied directly to the wine is so low that a malolactically active concentration of the organisms is only achieved at the indicated inoculation level.

The present invention provides, compared to the known methods, a significantly improved method of inducing malolactic fermentation in wine or fruit juice whereby it has become possible to achieve an effective malolactic fermentation herein wihtin a short period of time by inoculating wine or a fruit juice directly with a concentrated culture composition of malolactically active bacteria at an economically feasible concentration and accordingly, to avoid the tedious and costly processes of rehydration, activation, adaptation and/or expansion which are currently required with commercial malolactically active starter cultures.

SUMMARY OF THE INVENTION

Accordingly, the present invention relates in a first aspect to a method of inducing in a wine or a fruit juice the conversion of malic acid to lactic acid comprising the steps of selecting a strain of malolactically active bacteria, capable of starting malolactic fermentation in a wine or fruit juice when added directly thereto at a concentration of less than $10^7$ CFUs per mL, providing a concentrate of the selected malolactically active bacterium, introducing said concentrate directly into the wine or the fruit juice, and converting the malic acid while keeping the wine or the fruit juice under conditions which allow conversion of the malic acid to obtain a malolactically fermented wine or fruit juice having a content of malic acid which is at the most 0.5 g per L.

In a further aspect, the invention provides a selected strain of a malolactically active bacterium which, when it is added to a wine or fruit juice in a frozen or freeze-dried state at a concentration of CFUs which is in the range of $1 \times 10^6$ to $5 \times 10^7$ per mL of the wine or fruit juice, is capable of reducing at least 4 g of malic acid per L of wine or fruit juice to less then 0.5 g per L within a period of time which is at the most 15 days, said strain having at least one of following characteristics:

(a) capable of decarboxylating malic acid in wine at a pH of 3.2 or lower, (b) capable of decarboxylating malic acid in wine in the presence of 25 mg $SO_2$ per L or more, and (c) capable of decarboxylating malic acid in wine having an ethanol content of 10 vol % or higher.

(d) a survival rate of at least 80% when introduced directly into a wine having a pH of 3.2 or lower and containing at least 10 vol % ethanol, (e) a survival rate of at least 50% when introduced directly into a wine having a pH of 3.2 or lower and containing at least 25 mg $SO_2$ per L and at least 12 vol % ethanol, (f) resistant to attack by bacteriophages, (g) capable of retaining at least one of the characteristics (a) through (f) during propagation and concentration.

in a still further aspect, the invention relates to a concentrate of one or more of the selected strains of malolactically active bacteria as defined herein, and in another aspect there is provided a malolactic starter culture composition comprising a concentrate of selected malolactically active bacterial strain(s), as defined herein and at least one further ingredient selected from cryoprotectants, bacterial nutrients and bulking agents.

DETAILED DISCLOSURE OF THE INVENTION

The present invention relates in one aspect to a novel method of inducing the decarboxylation of malic acid to lactic acid in wines and fruit juices by direct inoculation of the wine or fruit juice with appropriately selected malolactically active bacteria.

In the present context, the term "wine" is used to describe a product resulting from an alcoholic fermentation of juice or must of grapes or of any other fruit or berries, whether the fermentation occurs spontaneously or it is obtained by the addition of a yeast culture.

A wine made from grapes may be a red wine, a white wine, a rosé wine, all of which may be in the form of sparkling wines.

The conditions prevailing in wine at the completion of the alcoholic fermentation is generally unfavorable for microbial growth. These adverse conditions include a pH typically being in the range of 2.8 to 4.0 such a pH of 3.2 or lower, an ethanol content which is typically in the range of 8 to 14 vol %, such as in the range of 10 to 12 vol %, a low content of nutrients such as carbon sources due to the depletion of the nutrients during the alcoholic fermentation. In addition, a sulphur-containing substance may have been added as a preservative to the must in an amount which is typically in the range of 5 to 70 mg per L including amounts of 25 mg of $SO_2$ as defined below per L in the fermented wine, or higher.

In this connection it should be noted that the addition of sulphur-containing substances to must is conventionally carried out by the addition of a sulphite or another water soluble sulphur-containing substance. In the fermenting must the sulphite is at least partially converted to $SO_2$, the extent of the conversion depending i.a. on the pH. Part of the generated $SO_2$ will be in the form of free molecules and part will be bound. In the art, the content of sulphur in must or wine is determined by measuring the total content of sulphur-containing substances as total $SO_2$. Accordingly, when used herein the term "$SO_2$" denotes the total content of sulphur determined according to the Rebelein method in which all sulphur-containing substances are converted to $SO_2$ before the measuring step.

These conditions in the wine, singly and in combination provides a rather hostile environment for bacteria, including malolactically active lactic acid bacteria. Such bacteria are primarily organisms belonging to the genera of Leuconostoc, Lactobacillus and Pediococcus. Among these genera of naturally occurring malolactically active bacteria, organisms belonging to Leuconostoc are generally most tolerant to low pH and they may grow at pH values below 3.3. At more moderate pH values such as of 3.6 and above, species of Lactobacillus and Pediococcus may grow as well. Within the Leuconostoc genus, the species *Leuconostoc oenos* is particularly adapted to grow in wines and this species is commonly used in commercial cultures as described above. Species of Lactobacillus which are of particular interest as malolactic starter culture organisms include *Lactobacillus casei, Lactobacillus brevis, Lactobacillus hilgardii* and *Lactobacillus plantarum.*

However, within a species of malolactically active bacteria there may exist differences between different isolates as to tolerance to one or more of the above-mentioned adverse conditions in wine. Accordingly, it may by applying appropriate methods be possible to select, within a species of malolactically active bacteria, isolates (strains) which are particularly tolerant to one or more of the adverse conditions. However, it is known in the art that when selecting a bacterial strain against one desired characteristic, such a strain will frequently be industrially less useful due to deficiencies as to other desired characteristics. E.g. may a strain selected on the basis of a high tolerance to acidic conditions be susceptible to moderate amounts of ethanol.

In a first step of the presently claimed method, a selection is carried out to obtain a strain of malolactically active bacteria, capable of starting malolactic fermentation in wine or fruit juice when added directly thereto at a concentration of less than $10^7$ CFUs per mL, the strain having at least one of the following characteristics:
(a) capable of decarboxylating malic acid in wine at a pH of 3.2 or lower,
(b) capable of decarboxylating malic acid in wine in the presence of 25 mg $SO_2$ per L or more,
(c) capable of decarboxylating malic acid in wine having an ethanol content of 10 vol % or higher,
(d) a survival rate of at least 80% when introduced into a wine having a pH of 3.2 or lower and containing at least 10 vol % ethanol,
(e) a survival rate of at least 50% when introduced into a wine having a pH of 3.2 or lower and containing at least 25 mg $SO_2$ per L and at least 12 vol % ethanol,
(f) resistant to attack by bacteriophages, or
(g) capable of retaining at least one of the characteristics (a) through (f) during propagation and concentration.

When the selection criteria as those defined above have been determined, appropriate selection procedures known per se in the art can readily be chosen. Initially, a large number of strains of malolactically active bacteria are isolated from different types of wines and preferably from a range of viticultural regions. Such isolates may subsequently be tested individually according to each of the above selection criteria, or a number of the isolates may more conveniently be combined and subjected to a first selection in a wine used as a growth medium in a turbidostat fermentor to obtain selection of strains which are capable of growing in a wine at a low pH and a high ethanol content.

When using such a turbidostat growth selection procedure, the mixture of isolates are inoculated into a fermentor and the biomass is kept constant by means of a turbidometer. The culture is fed a nutrient-enriched wine with an increasing concentration of ethanol and a decreasing pH. When the pH level and the ethanol concentration is so high that no further bacterial growth is possible, a sample of the culture is drawn and representative strains of viable malolactically active bacteria are isolated and characterized.

In a second selection step, the isolated, acid and ethanol tolerant strains are tested in wines having different compositions for the characteristics (a) through (f) as mentioned above. In a next step, chosen strains are subjected to fermentor propagation under normal production conditions in order to select strains which have an industrially feasible growth yield and which at the same time maintain the characteristics based on which they were selected.

In a final selection step, the strains which pass the preceding step is subjected to a down-stream process including at least one of the following steps: harvesting of cells from the culture medium, concentration of the cells, freezing of the concentrate or freeze-drying.

It will be understood that a selected strain should preferably have as many as possible of the above-defined characteristics (a) through (g). Accordingly, the selected strain is preferably one which has at least two of the characteristics, more preferably one having at least three of the characteristics and most preferably the strain is one which has all of the defined characteristics. In particular, the selected strain should in addition to other advantageous characteristics have a high rate of survival under the conditions as defined aboved. A high survival rate makes it possible to have the MLF started at the low CFU concentrations as defined above and allow the high proportion of surviving cells to enter the active growth phase and becoming malolactically active essentially momentaneously or within a short period of time such as within 1–3 days, thereby obtaining the malolactically fermented wine or fruit juice within the short periods of time as defined herein. It may be observed with cultures having a low survival rate and applied in high concentrations that although an initial conversion of malic acid takes place due to the release of malolactically active enzymes from the killed cells, the active growth phase is entered only after a prolonged lag phase of 5–10 days and accordingly, such cultures will not be suitable for obtaining a rapid MLF and particularly, these cultures will not result in a conversion of high amounts of malic acid wihtin an industrially acceptable period of time, such as it is obtained with the present selected strains.

In accordance with the invention, a suitable malolactically active bacterial strain is one selected from a species belonging to the genera of Leuconostoc, Lactobacillus and Pediococcus. When the strain is selected from a species of the Leuconostoc genus, the species is preferably *Leuconostoc oenos* such as a strain which is selected from the group consisting of DSM 7008, DSM 7009, DSM 7010, DSM 7011, DSM 7012, DSM 7013, DSM 7014 and DSM 7015. These 8 strains were deposited on Mar. 26, 1992 with Deutsche Sammlung von Mikroorganismen und Zellkulturen GmbH (German Collection of Microorganisms and Cell Cultures), Braunschweig, Germany.

In a second step of the method as claimed herein, there is provided a concentrate of the thus selected malolactically active strain. The concentrate is preferably one in which the number of colony forming units is in the range of $10^9$ to $10^{12}$ per g. In more preferred embodiments, the concentrate has a number of colony forming units which is in the range of $10^{11}$ to $10^{12}$ per g.

As an initial step in the obtainment of the concentrate, a chosen selected strain is propagated according to processes which are well-known in the art. Such processes include the step of cultivating the strain in a suitable fermentor vessel containing a suitable growth medium containing sufficient amounts of nutrients required for economically feasible growth yield of the particular strain. In accordance with the invention, a suitable growth medium for propagation of malolactically active bacteria contains as the major ingredient grape juice to which may be added yeast concentrate or extract, malic acid, a surface active substance such as Tween™ 80, a manganese salt, water and a vitamin mixture. In preferred embodiments of the invention, the pH in the growth medium is in the range of 4 to 6.

Subsequent to the above propagation step, the cell biomass is harvested e.g. by centrifugation whereby a concentrate of cells is obtained in the form of a slurry or a cell paste. Alternatively, the concentrate of cells may be obtained by a filtration process. Although such a fresh cell paste may be used to inoculate a wine or fruit juice, the bacterial concentrate is more conveniently provided in the form of a preserved concentrate, since the viability of cells in a cell paste concentrate will decrease rapidly and furthermore, a fresh cell paste will be prone to growth of contaminating microorganisms. In accordance with the invention, a concentrate may be preserved by freezing e.g. by dripping the paste into liquid nitrogen or by introducing the cell paste into a suitable freezing apparatus. In order to retain the viability of cells during freezing, the paste may be mixed with suitable cryoprotectants such as gelatine, prior to freezing. In a preferred embodiment of the invention, the concentrate is provided as a freeze-dried concentrate which is typically prepared by subjecting a frozen concentrate to a conventional freeze-drying process.

In a subsequent step of the claimed method, a concentrate of the selected malolactically active strain is inoculated directly into the malic acid-containing wine or fruit juice. In the present context, the term "inoculated directly" is used to describe that the concentrate as defined herein is added to the wine or fruit juice without any prior rehydration and/or activation step. As it has been explained above, the known commercial malolactic starter cultures for postalcoholic MLF all require that they are subjected to an adaptation step including an activation step and optionally (if they are in a freeze-dried state) an initial rehydration step, prior to inoculation. If such known cultures are inoculated directly, the viability of the cells is typically reduced by a factor of 100 to 1000.

The concentrate is added to the wine or the fruit juice in an amount which results in the introduction of a number of bacteria, calcutated on a CFU basis which is in the range of $10^5$ to $10^7$ per mL. The preferred inoculation rate depends on several factors including the amount of malic acid to be converted, the desired period for obtaining the malolactically fermented wine or fruit juice and the temperature conditions. A typical preferred inoculation rate will be in the range of $10^6$ to $10^7$ CFUs per mL and a more preferred range may be $5 \times 10^6$ to $1 \times 10^7$ CFUs per mL.

In the final step of the method as claimed herein, the malic acid is converted to lactic acid while keeping the inoculated wine or fruit juice under conditions which will allow the conversion to take place. In particular, it is required to keep the wine or the fruit juice at a temperature where the inoculated culture is malolactically active. The majority of malolactic bacteria will be active at temperatures in the range of about 12 to about 25° C. A typical temperature for storing wine undergoing malolactic fermentation will be in the range of about 15 to 22° C.

As mentioned above, the content of malic acid in a wine may vary, in particular according to the climatic conditions of the viticultural region. Typically, the malic acid content will be in the range of 2 to 10 g per L. In specific embodiments of the invention, the wine or fruit juice to be malolactically fermented as defined herein is one having a malic acid content of at least 4 g per L, such as at least 5.5 g per L. In accordance with the invention, a malolactically fermented wine or fruit juice containing less than 0.5 g malic acid per L should preferably be obtained from such a wine or fruit juice within a period of time which is at the most 15 days. In more preferred embodiments, the period of time is at the most 12 days and in still more preferred embodiments it is at the most 10 days such as at the most 8 days.

In particularly preferred embodiments of the present invention, the obtained malolactically fermented wine or fruit juice has a malic acid content which is at the most 0.1 g per L.

As mentioned above, the present invention relates in further aspects to a strain of a malolactically active bacterium which has been selected according to the methods and selection criteria as defined above and to a concentrate of such a selected strain as also defined above.

Finally, the present invention provides a malolactic starter culture composition comprising the concentrate as defined herein and at least one further ingredient selected from cryoprotectants, including as an example gelatine, bacterial nutrients and bulking agents.

Conveniently, the claimed composition is preserved to obtain a commercial product which has a suitable shelf-life when stored and distributed appropriately. Accordingly, the composition is suitably a frozen or a freeze-dried composition which has been prepared by subjecting a mixture of the bacterial concentrate and the further ingredient(s) to a freezing and/or freeze-drying process essentially in accordance with the above-mentioned processes used for the claimed concentrate.

Preferably, the composition is one having a content of colony forming units which is in the range of $10^9$ to $10^{12}$ per g, such as in the range of $10^{11}$ to $10^{12}$ per g.

In useful embodiments of the invention, the composition is one which when it is inoculated directly into a wine or a fruit juice containing at least 4 g of malic acid per L such as at least 5.5 g per L at a concentration of CFUs which is in the range of $5 \times 10^6$ to $5 \times 10^7$ per mL, results in a malolactically fermented wine containing at the most 0.5 g malic acid per L within a period of time which is at the most 15 days, preferably at the most 12 days and more preferably at the most 10 days such as at the most 8 days.

It may be advantageous to provide the claimed composition as a composition comprising a multiplicity of the hereindefined selected strains of malolactically active bacteria. Accordingly, in one embodiment the composition comprises such a multiplicity.

DESCRIPTION OF DRAWINGS

The invention is further explained below with reference to the drawings in which.

EXAMPLE 1

Survival and Growth of *Leuconostoc oenos* in an Experimental Wine

An experimental wine was prepared by yeasting a sterile Riesling grape juice originating from Germany, without the addition of sulphite. After completion of the alcoholic fermentation, the wine was sterile filtered and the resulting wine had the following composition:

| Ethanol | 11.5 vol % |
| Malic acid | 3.9 g/L |
| Residual sugar | 3.5 g/L |
| pH | 3.15 |

A culture of *Leuconostoc oenos* strain DSM 7008 was prepared, and the sterile wine was inoculated with (1) cells of the strain directly from the fermentate (i.e. the growth medium containing an outgrown culture of the strain), (2) a cell concentrate after centrifugation, (3) a cell concentrate to which cryoprotective agents had been added or (4) a freeze-dried composition of a cell concentrate with added cryoprotectants, respectively. The numbers of CFUs which were inoculated by the four mentioned forms of the strain varied between $3 \times 10^6$ and $7 \times 10^6$ per mL of the experimental wine.

The survival of the added bacteria in the wine kept at 20° C. was monitored over 3 days, samples being collected on day 2 and 3 and the number of CFUs herein being determined according to standard methods for determining viable counts of *Leuconostoc oenos*.

Figure 1:
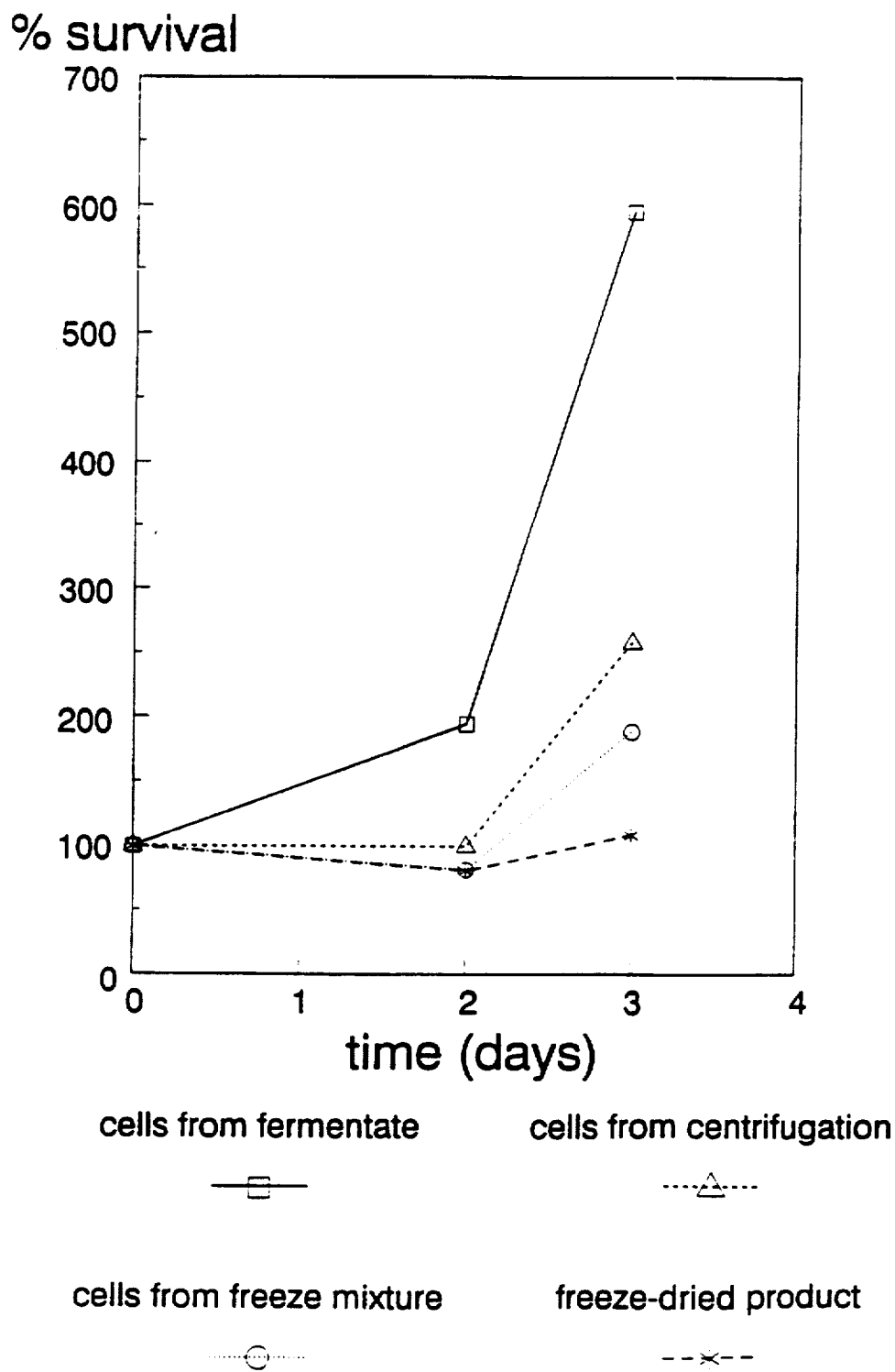
FIG. 1 shows the survival and growth (% CFU/mL) of *Leuconostoc oenos* strain DSM 7008 as fresh culture (fermentate) and as processed concentrates after direct inoculation into wine made from Riesling grape juice (11.5 vol % ethanol, 0 mg $SO_2$ per L, pH 3.15) of $3 \times 10^6$ to $7 \times 10^6$ per mL.
Figure 2A:
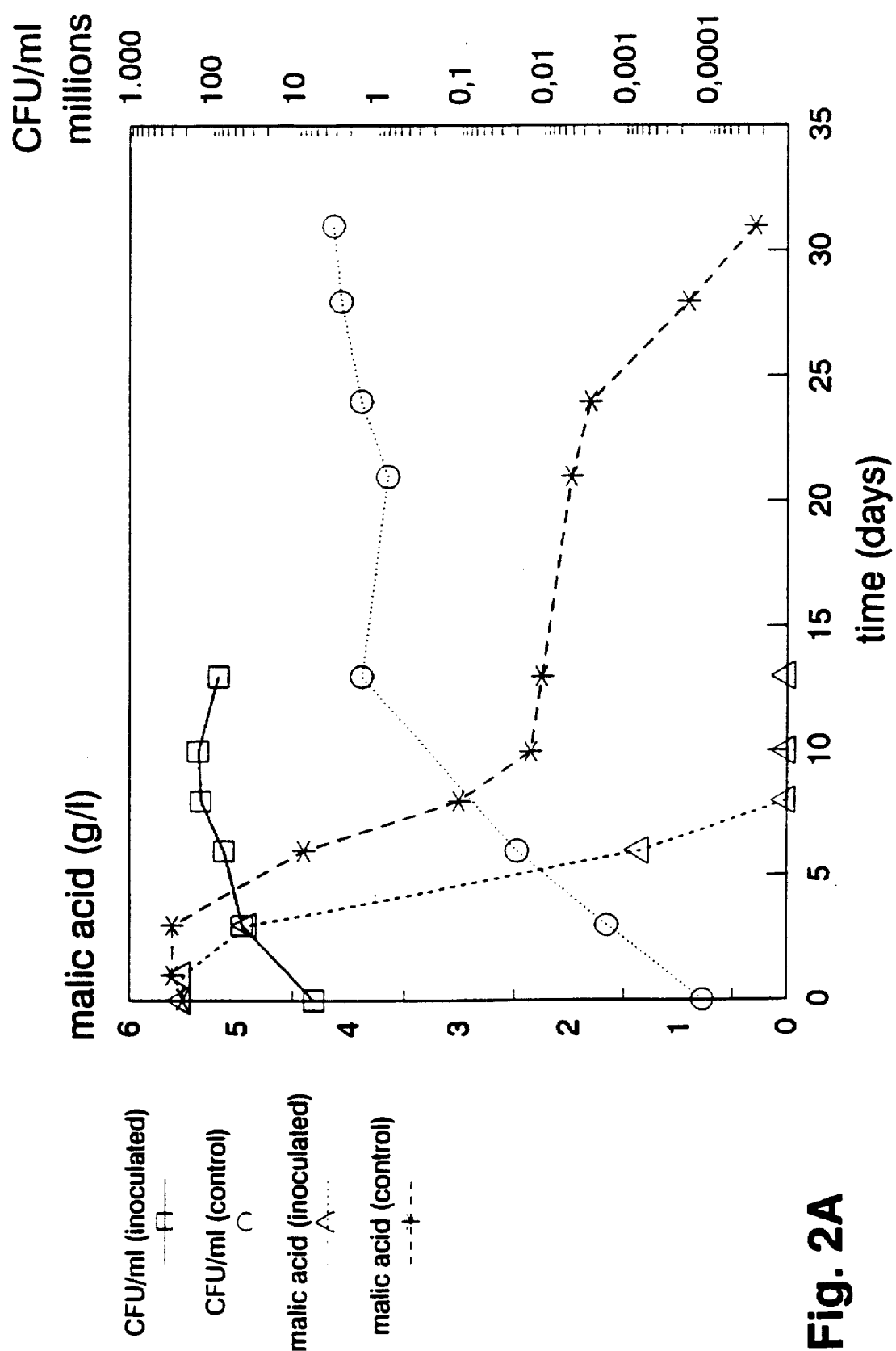
FIG. 2A shows the conversion of malic acid and CFU/mL of malolactically active bacteria in Chénin white wine (10.5 vol % ethanol, 16 mg $SO_2/L$, pH 3.5, 0.004 g/L of glucose and 0.003 g/L of fructose) kept at 18° C. in 5 L jars inoculated with a freeze-dried composition of *Leuconostoc oenos* strain DSM 7008, and in the same wine without inoculation.
Figure 2B:
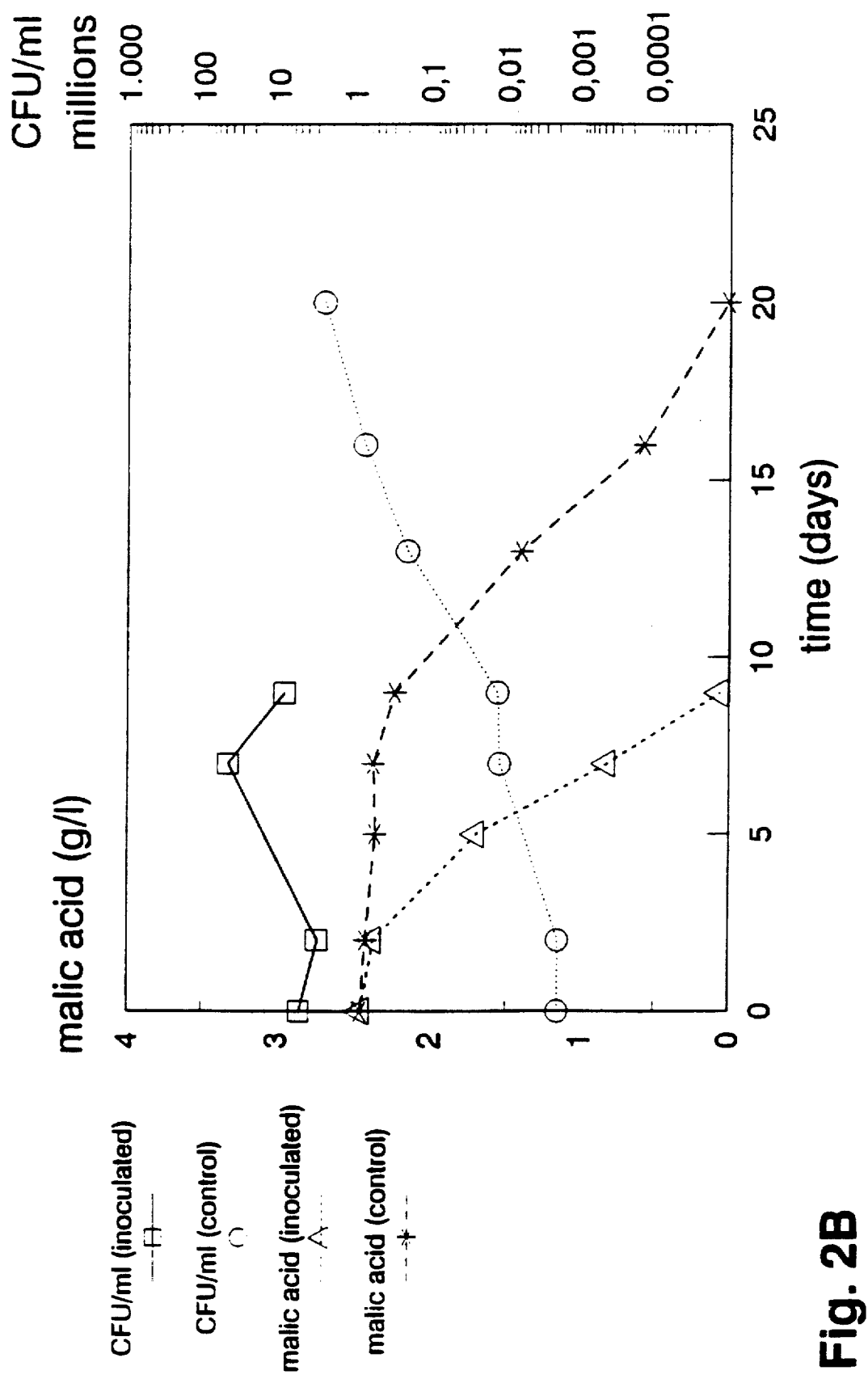
FIG. 2B shows the conversion of malic acid and CFU/mL of malolactically active bacteria in Cabernet Sauvignon red wine (11.0 vol % ethanol, 0 mg $SO_2/L$, pH 3.6, 0.11 g/L of glucose and 0.07 g/L of fructose) kept at 20° C. In 5 L jars inoculated with a freeze-dried composition of *Leuconostoc oenos* strain DSM 7008, and in the same wine without inoculation.
Figure 2C:
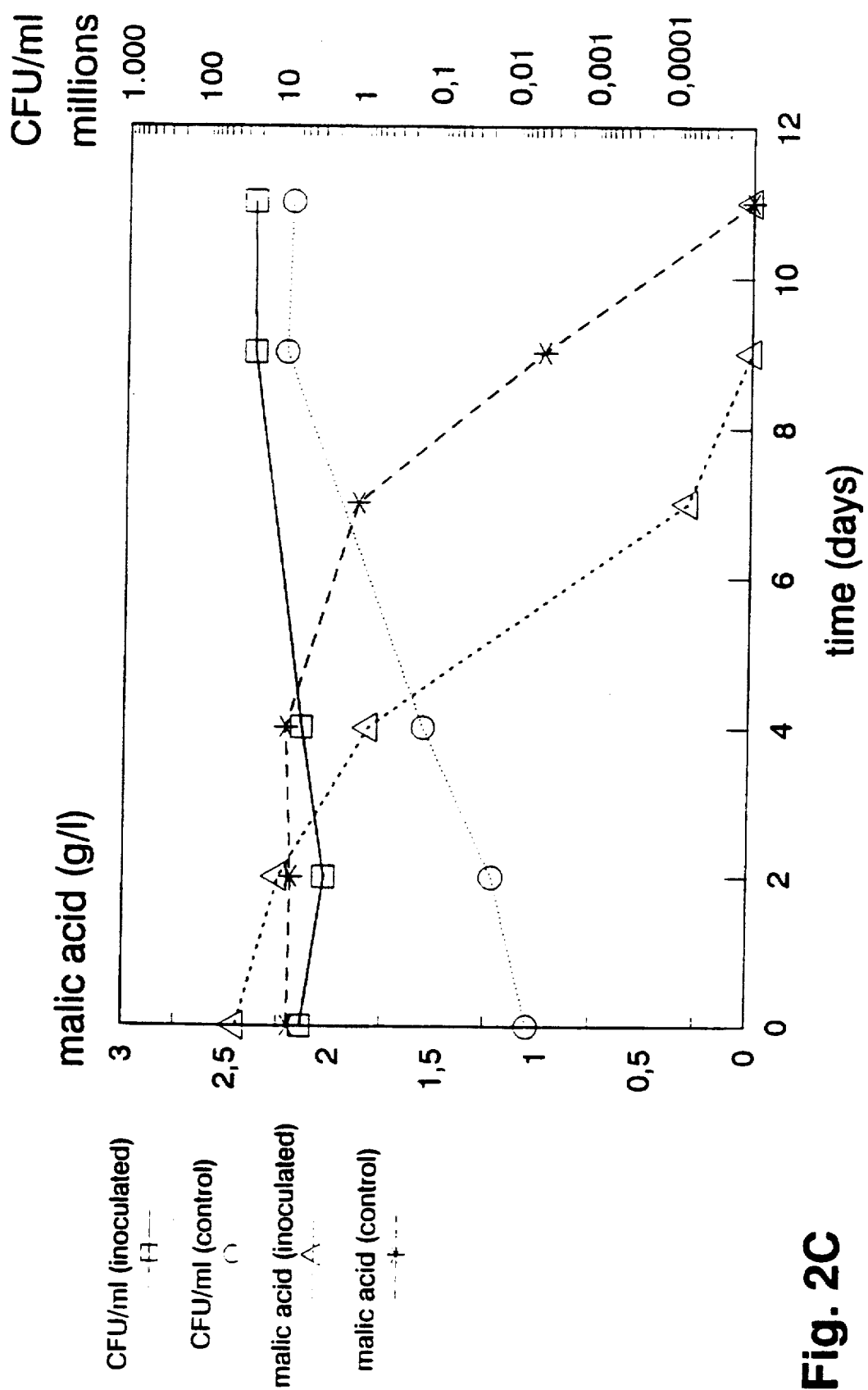
FIG. 2C shows the conversion of malic acid and CFU/mL of malolactically active bacteria in Cabernet Sauvignon red wine (11.3 vol % ethanol, 0 mg $SO_2/L$, pH 3.6, 0.11 g/L of glucose and 0.07 g/L of fructose) kept at 21° C. in 10.000 L insulated tanks inoculated with a freeze-dried composition of *Leuconostoc oenos* strain DSM 7008, and in the same wine without inoculation.
Figure 2D:
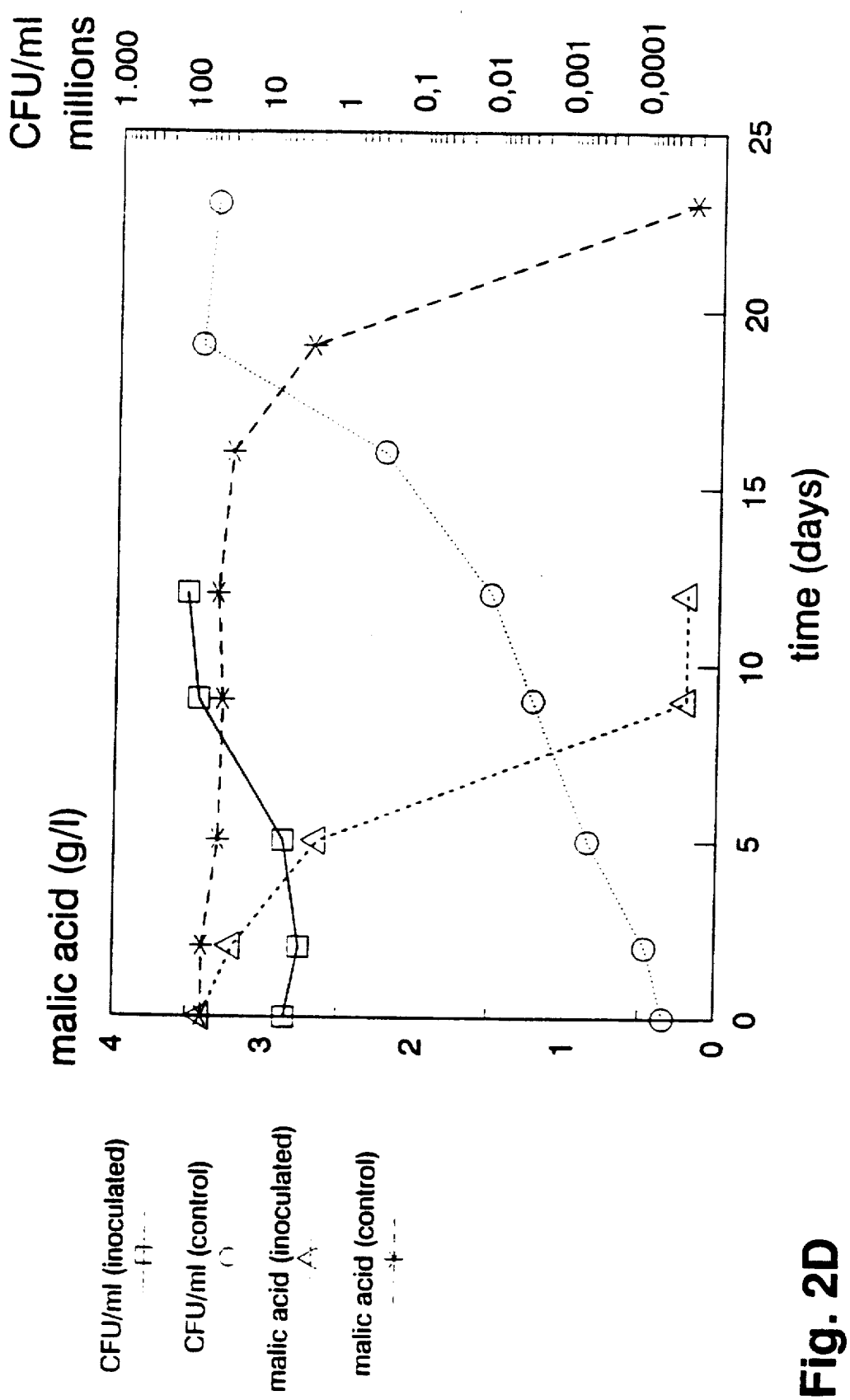
FIG. 2D shows the conversion of malic acid and CFU/mL of malolactically active bacteria in Cabernet Sauvignon red wine (11.8 vol % ethanol, 5 mg $SO_2/L$, pH 3.5, 0.3 g/L of glucose and 0.45 g/L of fructose) kept at 20° C. in 5 L jars inoculated with a freeze-dried composition of *Leuconostoc oenos* strain DSM 7008, and in the same wine without inoculation.
Figure 2E:
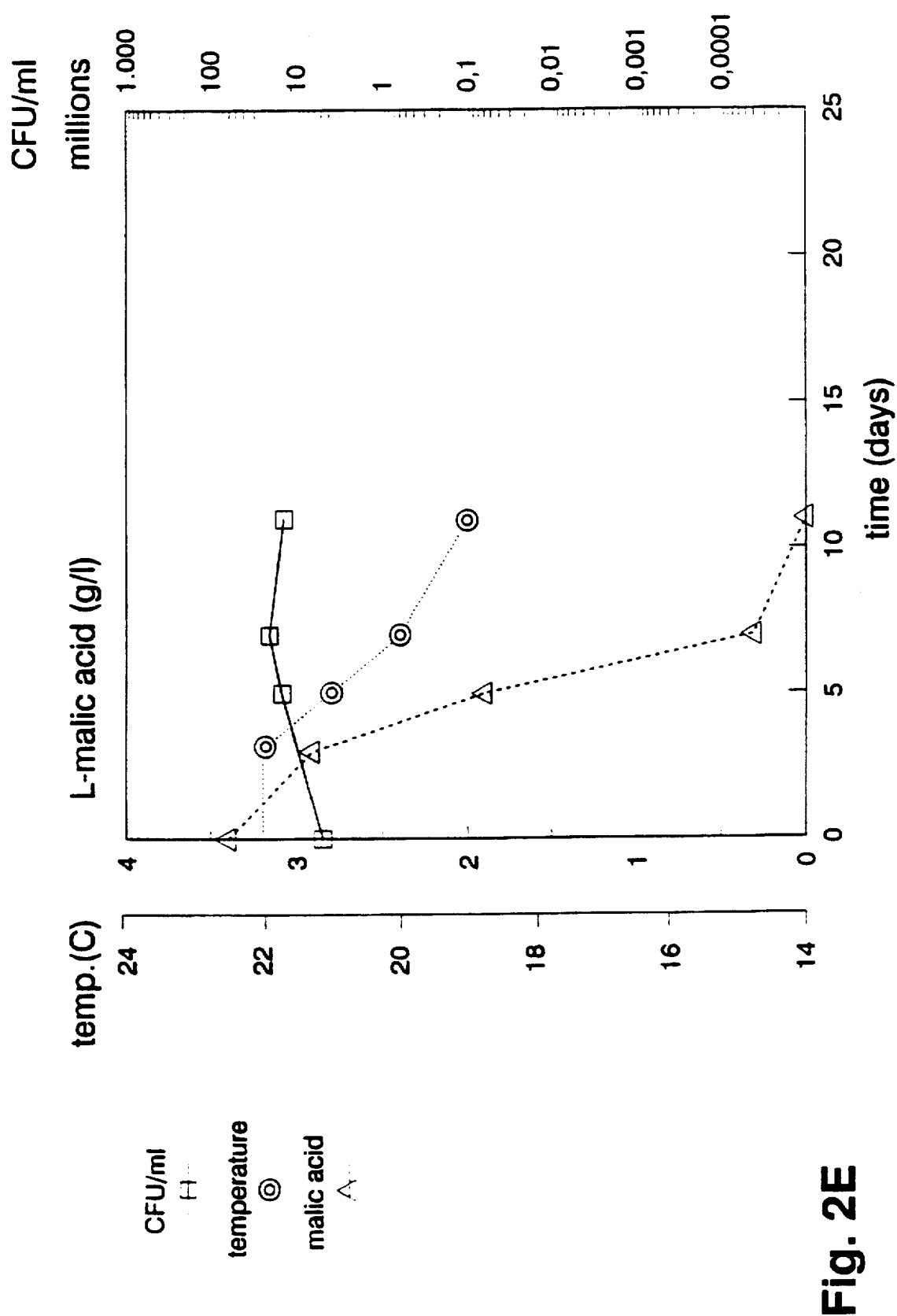
FIG. 2E shows the conversion of malic acid and CFU/mL of malolactically active bacteria in Cabernet Sauvignon red wine (11.8 vol % ethanol, 5 mg $SO_2/L$, pH 3.5, 0.3 g/L of glucose and 0.45 g/L of fructose) kept at 20° C. in 5 L jars inoculated with a freeze-dried composition of *Leuconostoc oenos* strain DSM 7008, and in the same wine without inoculation.
Figure 2F:
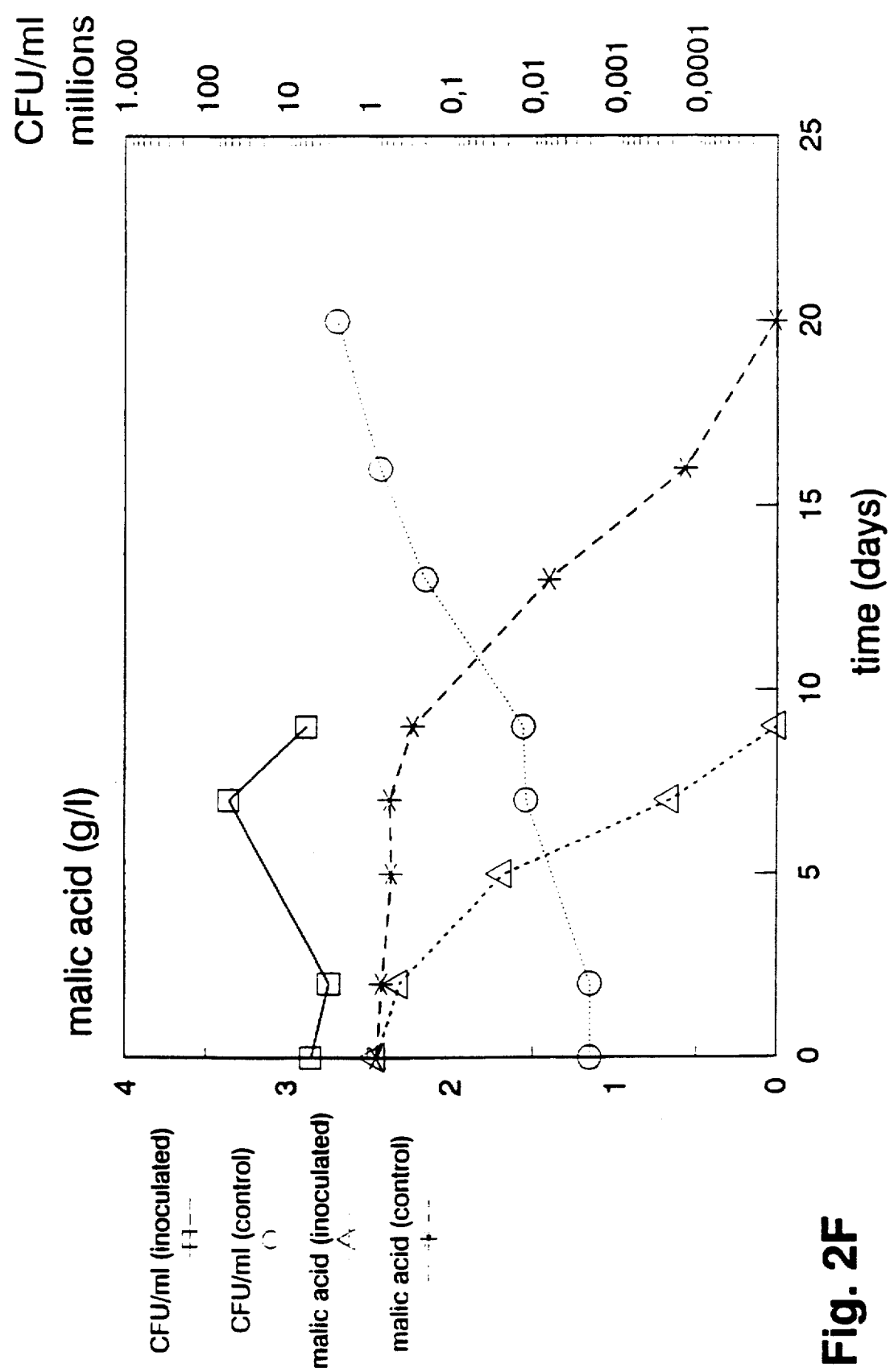
FIG. 2F shows the conversion of malic acid and CFU/mL of malolactically active bacteria in Cabernet Sauvignon red wine (11.0 vol % ethanol, 0 mg $SO_2/L$, pH 3.6, 0.11 g/L of glucose and 0.07 g/L of fructose) kept at 20° C. in 5 L jars inoculated with a freeze-dried composition of *Leuconostoc oenos* strain DSM 7015, and in the same wine without inoculation.
Figure 2G:
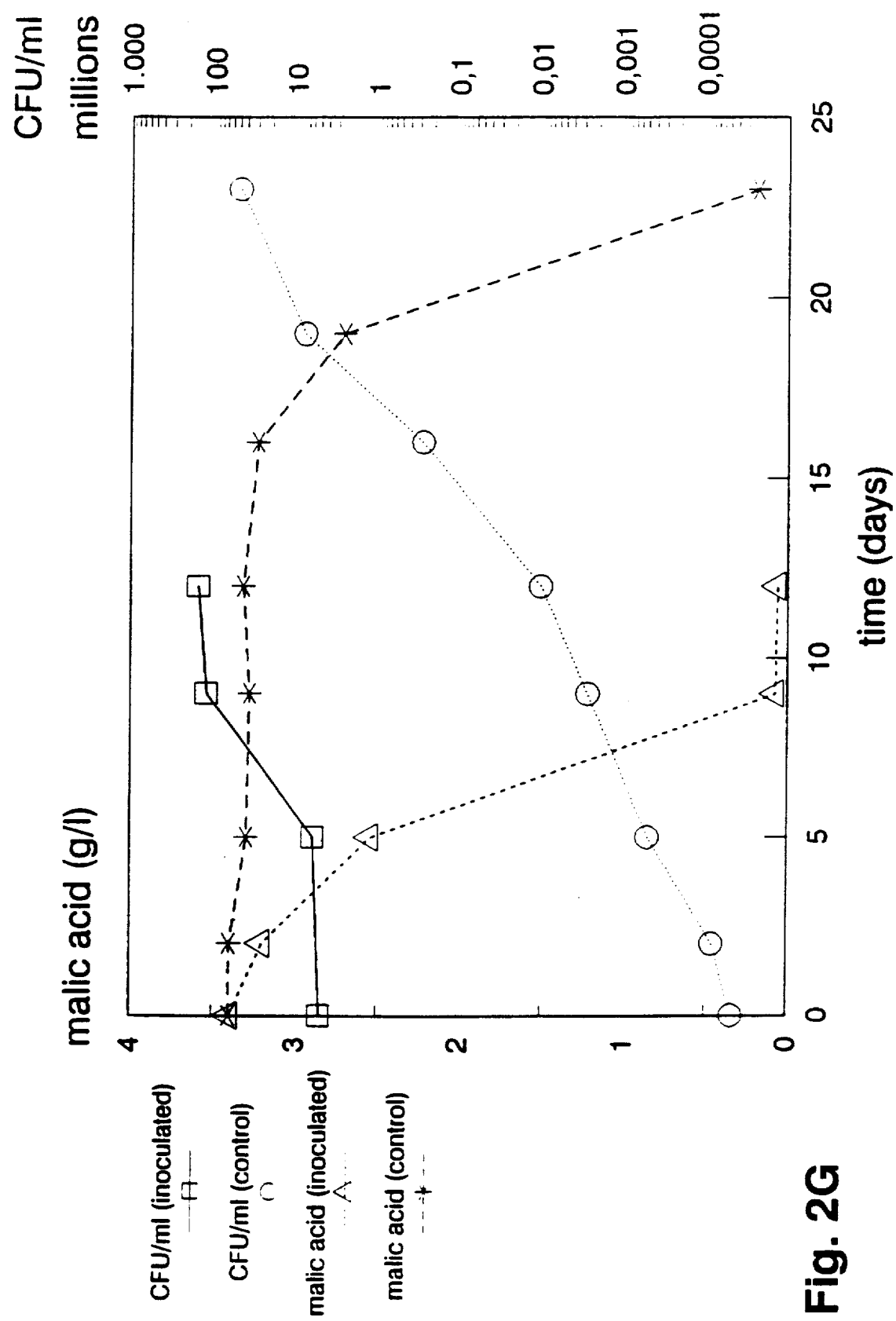
FIG. 2G shows the conversion of malic acid and CFU/mL of malolactically active bacteria in Cabernet Sauvignon red wine (11.8 vol % ethanol, 5 mg $SO_2/L$, pH 3.5, 0.3 g/L of glucose and 0.45 g/L of fructose) kept at 20° C. in 5 L jars inoculated with a freeze-dried composition of *Leuconostoc oenos* strain DSM 7015, and in the same wine without inoculation.
Figure 2H:
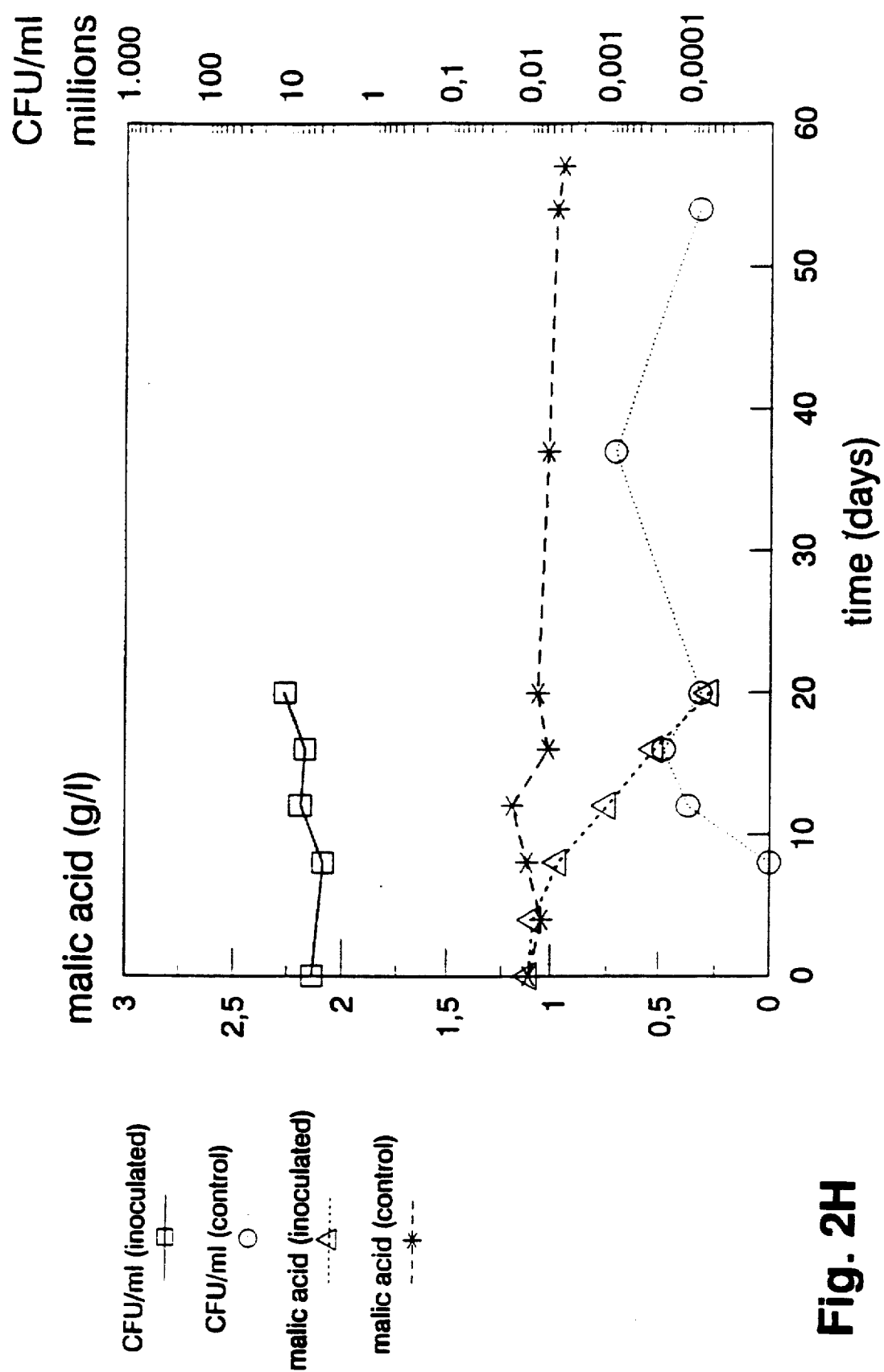
FIG. 2H shows the conversion of malic acid and CFU/mL of malolactically active bacteria in Cabernet Franc red wine (13.0 vol % ethanol, 2 mg $SO_2/L$, pH 3.4) kept at 20° C. in 5 L jars inoculated with a freeze-dried composition of *Leuconostoc oenos* strain DSM 7008, and in the same wine without inoculation.
Figure 2I:
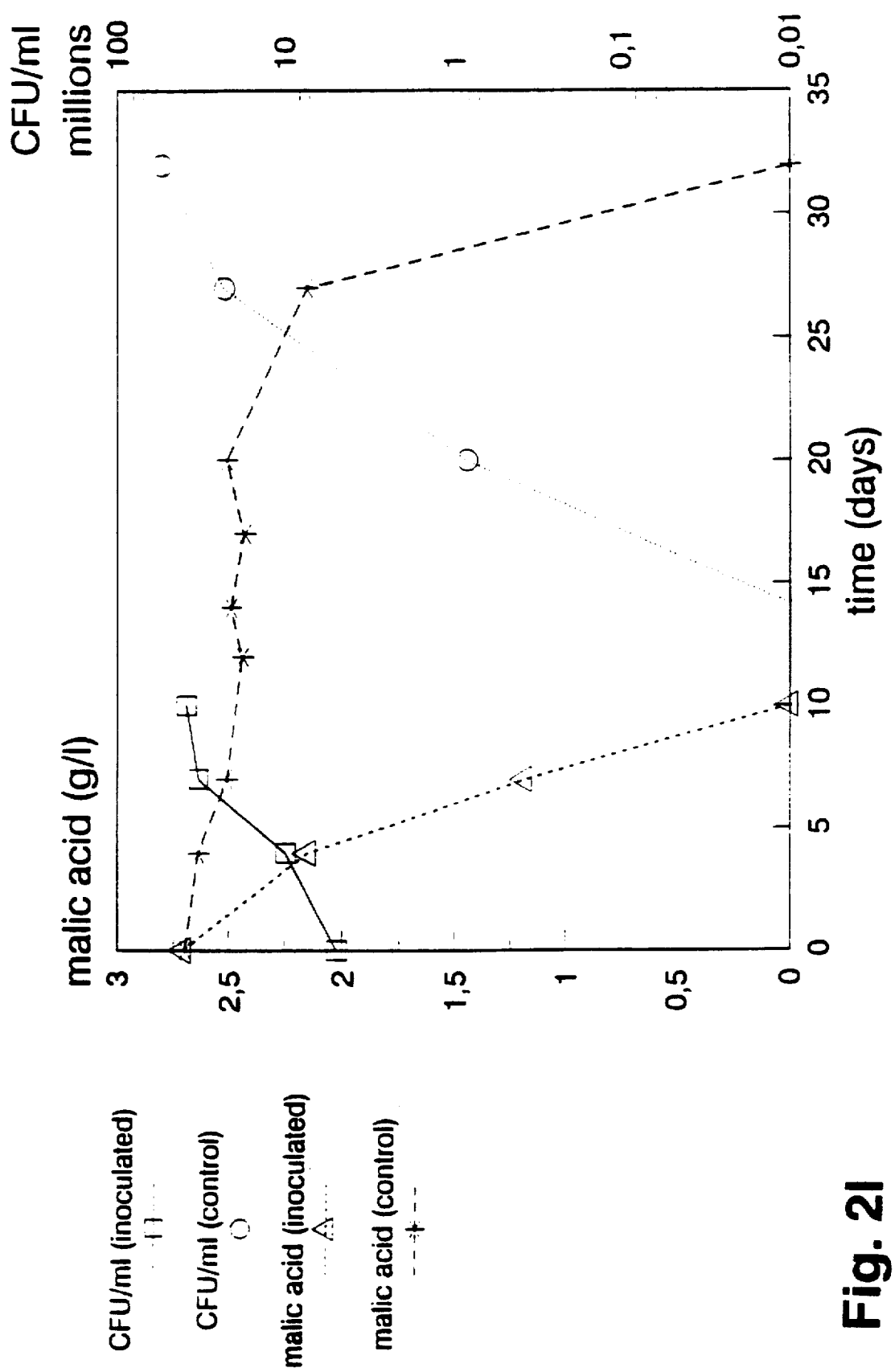
FIG. 2I shows the conversion of malic acid and CFU/mL of malolactically active bacteria in Semillon white wine (12.2 vol % ethanol, 26 mg $SO_2/L$, pH 3.2) kept at 19° C. in 5 L jars inoculated with a freeze-dried composition of *Leuconostoc oenos* strain, DSM 7008, and in the same wine without inoculation.

The results of this experiment are shown in FIG. 1 from which it appears that the bacteria when added in the form of a fermentate multiplied during the keeping time, with a factor of about 6. Bacteria added in the form of processed inocula showed a survival rate after 2 days which was in the range of 80% to 100% and during the next day the numbers of CFUs of these inocula increased by 10% to 60% relative to the initial numbers.

EXAMPLE 2

Induction of Malolactic Fermentation in Bordeaux Red Wines and White Wines by Direct Inoculation with *Leuconostoc oenos*-Containing Compositions The malolactic effect of freeze-dried compositions of two strains of *Leuconostoc oenos*, DSM 7008 and DSM 7015 were tested by direct inoculation into different wines. The study was carried out by inoculating wines in 5 L jars and in industrial scale by inoculating wines contained in 5.000 to 10.000 L tanks. The inoculum level was about $5\times10^6$ per mL of wine.

The study comprised the following experiments:

1. Inoculation with strain DSM 7008 of Chénin white wine from the Loire region contained in 5 L jars.
2. Inoculation with strains DSM 7008 and DSM 7015 of Cabernet Sauvignon red wine from Graves in the Bordeaux region, kept in 5 L jars and additionally with DSM 7008 in a 10.000 L tank.
3. Inoculation with strains DSM 7008 and DSM 7015 of Cabernet Sauvignon red wine from Premiéres Côtes de Bordeaux contained in 5 L jars and additionally with strain DSM 7008 in a 5.000 L tank. This wine had a content of ethanol of 11.8 vol % and a $SO_2$ content of 5 mg per L and a pH of 3.5.
4. Inoculation with strain DSM 7008 of Cabernet-Franc red wine from Premiéres Côtes de Bordeaux, kept in 5 L jars.
5. Inoculation with strain DSM 7008 of Semillon white wine from Côtes de Montravel in the Bordeaux region, kept in 5 L jars.

The tested wines had an initial content of malic acid in the range of 3 to 5.5 g per L, and the content of $SO_2$ was in the range of 0 to 26 mg per L. In all of the inoculated wines the malolactic fermentation occurred at a rate which resulted in a substantially complete disappearance of malic acid within 8 to 20 days. The survival rate of the inoculated bacteria was 90 to 100% in the test wines and in most wines an increase of CFUs up till about $10^8$ per mL occurred during the malolactic fermentation period.

We claim:

1. A biologically pure malolactically active *Leuconostoc oenos* strain which is selected from the group consisting of DSM 7008, DSM 7009, DSM 7010, DSM 7011, DSM 7012, DSM 7013, DSM 7014 and DSM 7015.

2. A biologically pure malolactically active *Leuconostoc oenos* strain which has all of the identifying characteristics of a strain selected from the group consisting of DSM 7008, DSM 7009, DSM 7010, DSM 7011, DSM 7012, DSM 7013, DSM 7014, and DSM 7015.

3. A concentrate of a biologically pure *Leuconostoc oenos* strain selected from the group consisting of DSM 7008, DSM 7009, DMS 7010, DSM 7011, DSM 7012, DSM 7013, DSM 7014, and DSM 7015.

4. A freeze-dried malolactic starter culture composition, comprising:

(a) a concentrate of a biologically pure *Leuconostoc oenos* strain selected from the group consisting of DSM 7008, DSM 7009, DSM 7010, DSM 7011, DSM 7012, DSM 7013, DSM 7014, and DSM 7015; and (b) at least one ingredient selected from the group consisting of cryoprotectants, bacterial nutrients and bulking agents.

5. A composition according to claim 4, wherein the cryoprotectant is gelatine.

\* \* \* \* \*